United States Patent
McCabe et al.

(10) Patent No.: US 7,277,754 B2
(45) Date of Patent: Oct. 2, 2007

(54) METHOD AND SYSTEM FOR REMOVING PACING ARTIFACTS FROM SUBCUTANEOUS ELECTROCARDIOGRAMS

(75) Inventors: Aaron McCabe, Minneapolis, MN (US); David J. Yonce, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 44 days.

(21) Appl. No.: 10/746,855

(22) Filed: Dec. 24, 2003

(65) Prior Publication Data

US 2005/0149134 A1    Jul. 7, 2005

(51) Int. Cl.
*A61N 1/36* (2006.01)
(52) U.S. Cl. .............. 607/9; 607/32; 600/523; 600/509; 128/923
(58) Field of Classification Search .......... 607/32, 607/60; 128/901, 923; 600/517, 521
See application file for complete search history.

(56) References Cited

U.S. PATENT DOCUMENTS

| | | | |
|---|---|---|---|
| 4,000,461 A | 12/1976 | Barber et al. | |
| 4,333,470 A | 6/1982 | Barthel | |
| 4,336,810 A | 6/1982 | Anderson et al. | |
| 4,539,999 A * | 9/1985 | Mans | 600/509 |
| 4,585,004 A | 4/1986 | Brownlee | |
| RE32,378 E | 3/1987 | Barthel | |
| 4,680,708 A | 7/1987 | Ambos et al. | |
| 4,838,278 A | 6/1989 | Wang et al. | |
| 4,884,345 A | 12/1989 | Long | |
| 5,127,401 A | 7/1992 | Grevious et al. | |
| 5,184,615 A | 2/1993 | Nappholz et al. | |
| 5,240,009 A | 8/1993 | Williams | |
| 5,309,919 A | 5/1994 | Snell et al. | |
| 5,331,966 A | 7/1994 | Bennett et al. | |
| 5,379,775 A | 1/1995 | Kruse | |
| 5,448,997 A | 9/1995 | Kruse et al. | |
| 5,487,755 A | 1/1996 | Snell et al. | |
| 5,503,160 A * | 4/1996 | Pering et al. | 600/519 |
| 5,630,425 A | 5/1997 | Panescu et al. | |
| 5,682,902 A | 11/1997 | Herleikson | |
| 5,683,425 A | 11/1997 | Hauptmann | |
| 5,697,959 A | 12/1997 | Poore | |
| 5,776,168 A | 7/1998 | Gunderson | |
| 5,795,303 A * | 8/1998 | Swanson et al. | 600/509 |
| 5,902,324 A * | 5/1999 | Thompson et al. | 607/9 |
| 5,954,662 A | 9/1999 | Swanson et al. | |
| 5,974,341 A | 10/1999 | Er et al. | |
| 6,169,918 B1 * | 1/2001 | Haefner et al. | 600/509 |
| 6,477,404 B1 | 11/2002 | Yonce et al. | |
| 6,745,068 B2 * | 6/2004 | Koyrakh et al. | 600/515 |
| 2003/0050563 A1 * | 3/2003 | Suribhotla et al. | 600/509 |
| 2003/0208238 A1 * | 11/2003 | Weinberg et al. | 607/9 |
| 2004/0127950 A1 * | 7/2004 | Kim et al. | 607/27 |
| 2005/0197674 A1 | 9/2005 | McCabe et al. | |
| 2006/0095083 A1 | 5/2006 | Zhang et al. | |

* cited by examiner

*Primary Examiner*—Robert E. Pezzuto
*Assistant Examiner*—Tammie Heller
(74) *Attorney, Agent, or Firm*—Schwegman, Lundberg, Woessner, & Kluth, P.A.

(57) ABSTRACT

An implantable cardiac rhythm management device is configured to remove pacing artifacts from recorded electrograms by a subtraction method. A template waveform representing a recorded pace without accompanying cardiac electrical activity is generated. Such a pacing pulse template is then aligned with the instant at which a pace is delivered and subtracted from the recorded electrogram in order to remove the pacing artifact.

18 Claims, 3 Drawing Sheets

METHOD AND SYSTEM FOR REMOVING PACING ARTIFACTS FROM SUBCUTANEOUS ELECTROCARDIOGRAMS

FIELD OF THE INVENTION

This invention pertains to cardiac rhythm management devices such as pacemakers and implantable cardioverter/defibrillators.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Pacing therapy may also be used in treatment of cardiac conduction disorders in order to improve the coordination of cardiac contractions, termed cardiac resynchronization therapy. Other cardiac rhythm management devices are designed to detect atrial and/or ventricular tachyarrhythmias and deliver electrical stimulation in order to terminate the tachyarrhythmia in the form of a cardioversion/defibrillation shock or anti-tachycardia pacing. Certain combination devices may incorporate all of the above functionalities. Any device with a pacing functionality will be referred to herein simply as a pacemaker regardless of other functions it may be capable of performing.

Cardiac rhythm management devices such as described above monitor the electrical activity of heart via one or more sensing channels so that pacing pulses or defibrillation shocks can be delivered appropriately. Such sensing channels include implanted leads which have electrodes disposed internally near the heart, which leads may also be used for delivering pacing pulses or defibrillation shocks. The signals generated from the sensing channels are intra-cardiac electrograms and reflect the time course of depolarization and repolarization as the heart beats, similar to a surface electrocardiogram (ECG). Implantable devices may also incorporate one or more subcutaneously disposed electrodes (e.g., on the surface of the device housing) into a sensing channel for generating an electrogram signal, referred to herein as a subcutaneous ECG. A subcutaneous ECG is more similar in its morphology characteristics to a surface ECG than is an intra-cardiac electrogram. The electrogram signals generated from the sensing channels of an implanted device, whether an intra-cardiac electrogram or a subcutaneous ECG, may be transmitted wirelessly to an external device where they can be displayed and analyzed in much the same manner as a surface electrocardiogram (ECG).

A problem that arises with using electrogram signals generated by pacemakers for morphology analysis, however, is that pacing pulses produce artifacts which interfere with the signal which actually represents the electrical activity of the heart. Electrograms generated during paced cardiac cycles are sometimes referred to as evoked response electrograms. The usual method by which a pacemaker deals with evoked response electrogram signals is by temporarily disabling, or blanking, its sensing channels during the pace in order to avoid saturation of the sense amplifiers. Such blanking periods, however, remove valuable information from the electrogram signal. External devices for recording electrograms from skin electrodes (i.e., surface ECG's) have been developed which employ digital filtering techniques with a high sampling rate to remove the pacing artifacts from evoked response electrograms. Such techniques, however, may introduce other distortion into the signal and are computationally expensive so that they may not be practical in an implantable device with limited processing capability. The present invention relates to an improved means for dealing with the problem of pacing artifacts in a computationally efficient manner.

SUMMARY

The present invention relates to a method or system which may be implemented in an implantable cardiac rhythm management device for removing pacing artifacts from an electrogram signal, particularly from a subcutaneous ECG. In accordance with the invention, a pacing template is generated by recording an electrogram during a pace which fails to capture the heart and produces no cardiac electrical activity such as a pace delivered while the heart is refractory. The pacing template thus represents the electrical signal produced by the pace alone and, when subtracted from an electrogram recorded during a paced cardiac cycle, effectively removes the pacing artifact.

DETAILED DESCRIPTION

As described above, the present invention relates to a method or system for removing pacing artifacts from evoked response electrograms by a subtractive method. In order to remove a pacing artifact, a pacing template representing the electrical signal of a pace without any accompanying cardiac electrical activity is subtracted from an evoked response electrogram recorded during a paced cardiac cycle. In an exemplary embodiment, the method is implemented by appropriate programming of the controller of an implantable cardiac rhythm management device as described below.

1. Exemplary Implantable Device Description

Cardiac rhythm management devices are implantable devices that provide electrical stimulation to selected chambers of the heart in order to treat disorders of cardiac rhythm. Such devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site.

Figure 1:
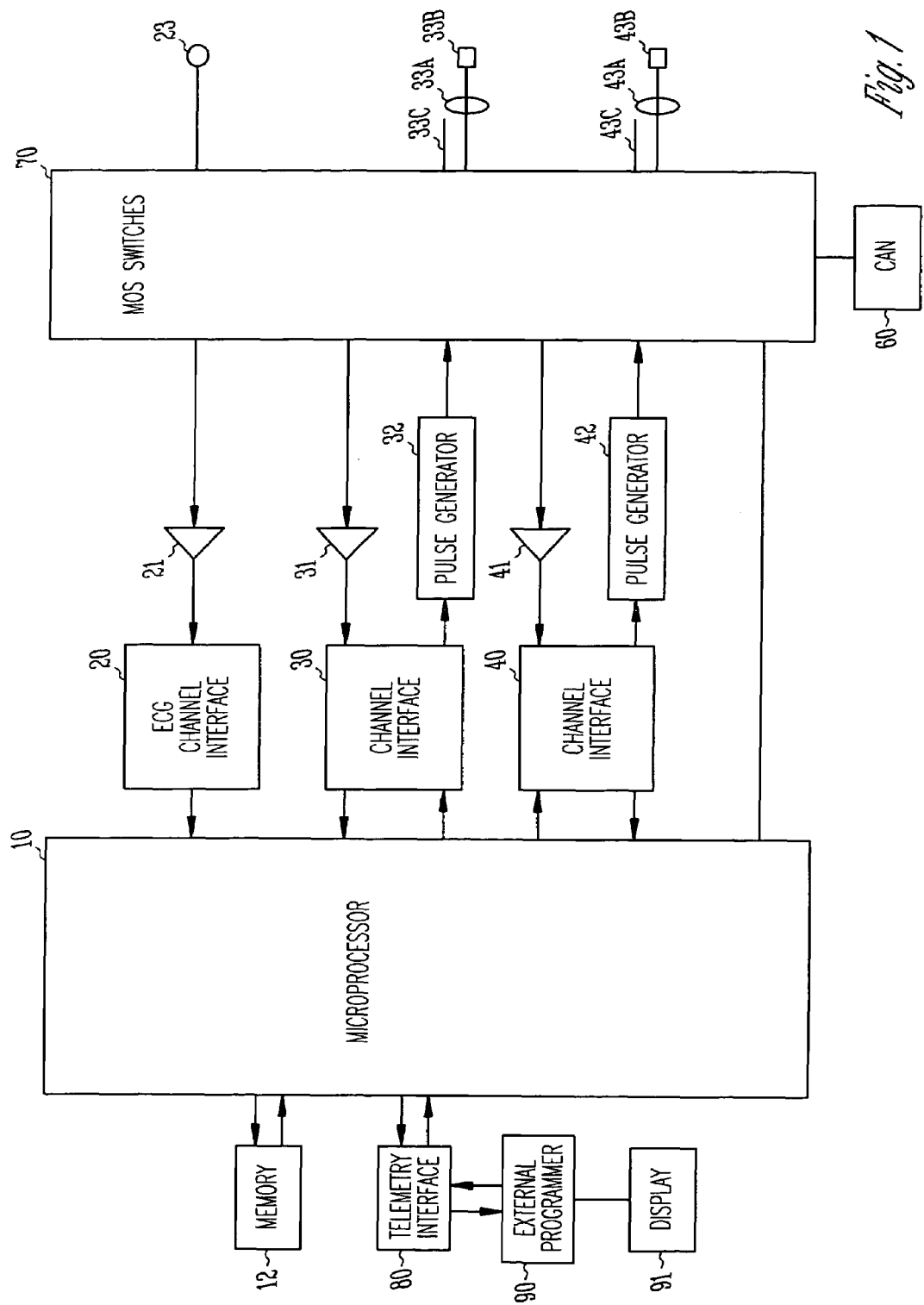
FIG. 1 is a block diagram of an exemplary cardiac rhythm management device for practicing the present invention.

A block diagram of an implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external programmer 90 or other device via a wireless telemetry link. The external programmer 90 is a computerized device which can be used to program the implantable device and received data from it. A display 91 or other output means allows the external programmer to display received data, such as recorded or near real-time electrograms.

The embodiment shown in FIG. 1 has two sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. In an example configuration, one sensing/pacing channel includes ring electrode 43a and tip electrode 43b of bipolar lead 43c, sense amplifier 41, pulse generator 42, and a channel interface 40 while another sensing/pacing channel includes ring electrode 33a and tip electrode 33b of bipolar lead 33c, sense amplifier 31, pulse generator 32, and a channel interface 30. The channels may be configured as either atrial or ventricular channels. A dedicated subcutaneous ECG sensing channel is also shown made up of a channel interface 20, sense amplifier 21, and electrode 23 which can be disposed subcutaneously for generating a subcutaneous ECG. In certain devices, the ECG electrode 23 is mounted on the device housing. Also, more than one subcutaneous ECG electrodes may be provided. The switch matrix may configure the sensing vector of a subcutaneous ECG channel by referencing the electrode 23 to the device housing, or can, or to other subcutaneous electrodes.

The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator (not shown) may also be interfaced to the controller for delivering defibrillation shocks between an electrode and the housing, or can, 60 as selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing, or can, 60 (or another electrode) by the switch matrix 70.

The controller 10 controls the overall operation of the device in accordance with programmed instructions stored in memory and with information derived from the sensing channels. The voltages sensed by the sensing electrodes are electrogram signals that are analogous to a surface ECG and provide a temporal record of cardiac depolarization and repolarization that occurs during either intrinsic or paced beats. The sensing circuitry of the pacemaker generates atrial and ventricular senses when voltages sensed by the electrodes of a particular channel exceed a specified threshold. A ventricular sense would correspond to an R wave on an ECG, and an atrial sense would correspond to a P wave. The controller 10 interprets sense signals from the sensing channels in order to detect arrhythmias and to control the delivery of paces in accordance with a pacing algorithm that employs such senses to trigger or inhibit pacing. The electrogram signals can also be digitized and recorded (i.e., stored in memory) by the controller and then either transmitted via a telemetry link 80 to an external programmer or maintained in memory or other storage medium for later transmission. The patient's cardiac activity may thus be observed in real-time or over a selected historical period.

An electrogram signal which is recorded by an implantable device in order to approximate a surface ECG for morphology analysis is preferably obtained by a dedicated sensing channel with a subcutaneous ECG electrode 23, referred to herein as a subcutaneous ECG channel. A sensing channel may also be used to record an intra-cardiac electrogram for purposes of morphology analysis. It is preferable for such a sensing channel to employ unipolar sensing such that the sensing vector is between the ECG electrode and the device housing, or can, (or another distantly disposed electrode or electrodes). A large unipolar vector "sees" a larger volume of the myocardium, and changes in the depolarization pattern of the heart will be more readily reflected in an electrogram generated by such a vector. Another convenient sensing vector for this purpose is the shock vector that the device normally uses for delivering cardioversion/defibrillation shocks.

2. Removing Pacing Artifact from-Recorded Electrograms

The efficacy of an independent sensing channel in recording an electrogram signal for morphology analysis, such as a subcutaneous ECG, depends upon its ability to resolve high fidelity signals at all times, independent of the normal pacing activities of the device. This is especially important when it is desired to record an electrogram during a specific period of time or to wirelessly transmit an electrogram in near real time to an external monitoring device. When the sensing vector for recording the electrogram includes the device housing, however, unipolar pacing can interfere with the recorded electrogram signal if it is not accommodated for. Bipolar pacing can also interfere with the electrogram signal, although to a lesser extent.

A high fidelity recording is required for an electrogram which is to be used as a surrogate for an ECG and morphologically analyzed. Sensing without compensation or blanking during the display of a subcutaneous ECG signal, however, has the potential to create unwanted and confusing artifacts in the signal for a clinician viewing the signal or for algorithms which analyze the signal's morphology. Since the sensing channel is filtered, a pacing spike has the tendency to spread out and affect a significant portion of the signal. Simple blanking (such as averaging-and-hold) is undesirable since there is important cardiac activity during pacing. By removing pacing spikes from an electrogram signal by the subtractive method described herein, high fidelity recording and display of a subcutaneous ECG can occur without the need for blanking.

In accordance with the present invention, pacing artifacts are removed from an electrogram such as a subcutaneous ECG by subtracting a pacing template representing the electrical signal produced by a pace alone from each portion of an electrogram where a pace occurs. The pacing template may be generated by pacing a cardiac chamber (i.e., an atrium or a ventricle) shortly after a paced or intrinsic beat during the time when the chamber is refractory and recording the resulting signal from the subcutaneous ECG channel with the amplifiers set at a low gain in order to avoid saturation. To record an electrogram during a paced cycle, the amplifier gain of the subcutaneous ECG channel is similarly set at a low gain shortly before the pace, and the pacing template is then subtracted out of the recorded signal. The subtraction procedure is normally performed in the digital domain with the pacing template aligned with the instant at which a pace occurs in the evoked response electrogram. Samples of the pacing template are then subtracted from corresponding samples of the evoked response electrogram to result in an electrogram signal without the pacing artifact. Since an electrogram signal recorded over a period of time may include both paced and intrinsic (i.e., non-paced) cycles, the samples of an electrogram recorded during paced cycles may be multiplied by a proportionality factor or otherwise processed to compensate for their being recorded at a lower gain setting than samples recorded during intrinsic cycles. A marker signifying when the pace occurred may also be inserted into the displayed electrogram. The present invention thus allows a real-time subcutaneous ECG to be displayed without interruption. This is possible because the subcutaneous ECG system is located in the implantable device and the device is aware of when it is pacing.

In one embodiment, the subtraction procedure is implemented entirely in the programming of the implantable device so that one or more cycles of electrograms are recorded by the device, the subtraction procedure performed for each paced cycle to remove the pacing artifact, and the resulting signal is then stored in memory or transmitted to an external device over a telemetry link. Rather than subtracting the pacing template from a recorded electrogram, the subtraction procedure may alternatively be performed as the samples of the electrogram signal are collected so that a corresponding template sample is subtracted from each sample of a paced cycle electrogram before it is stored in memory. The invention thus allows a sensed subcutaneous ECG system to record and/or transmit continuously without interruption due to the pacing spikes.

In another embodiment, the implantable device may transmit the pacing template which it has generated to an external device such as an external programmer via telemetry. The implantable device then transmits the electrogram signal to the external device (either after storage in the memory of the implantable device or in near real-time) where the external device then subtracts the pacing template from the portions of the electrogram representing paced cycles. In this embodiment, the implantable device also transmits to the external device a signal indicating the instants at which paces occur in order to identify evoked response electrograms and provide an alignment point for the pacing template.

Figure 2:
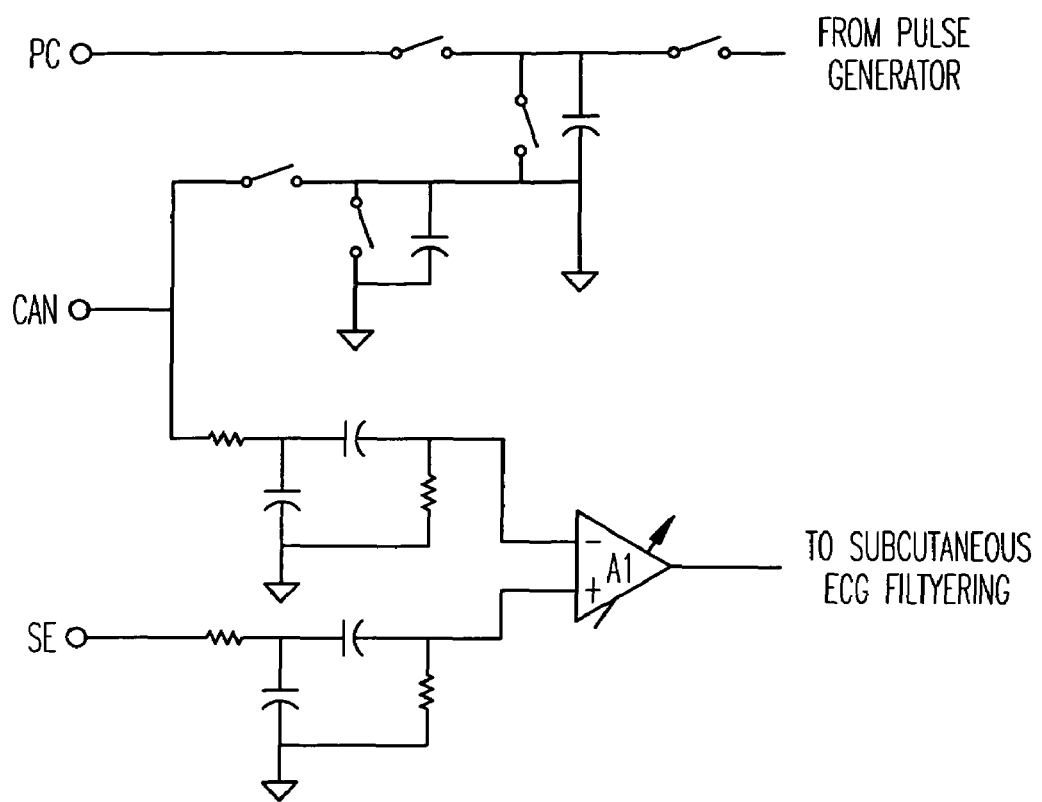
FIG. 2 is a schematic diagram of a pacemaker output stage and ECG sensing channel configured for unipolar pacing and sensing, respectively.

FIG. 2 shows a functional schematic diagram of a pacing pulse output stage and a subcutaneous ECG sensing channel as could be configured by the switch matrix 70 in FIG. 1. The ECG sensing channel includes a sensing amplifier A1 and a sensing electrode SE, and the output stage includes a pacing cathode PC which receives pacing pulses from a pulse generator. The device housing or can, designated as CAN in the figure, provides a common ground for both subcircuits. The sensing amplifier A1 has an adjustable gain which may be set by the controller. During generation of the pacing template and during collection of evoked response electrogram samples, the gain of amplifier A1 is set to a low value to avoid saturation.

Figure 3:
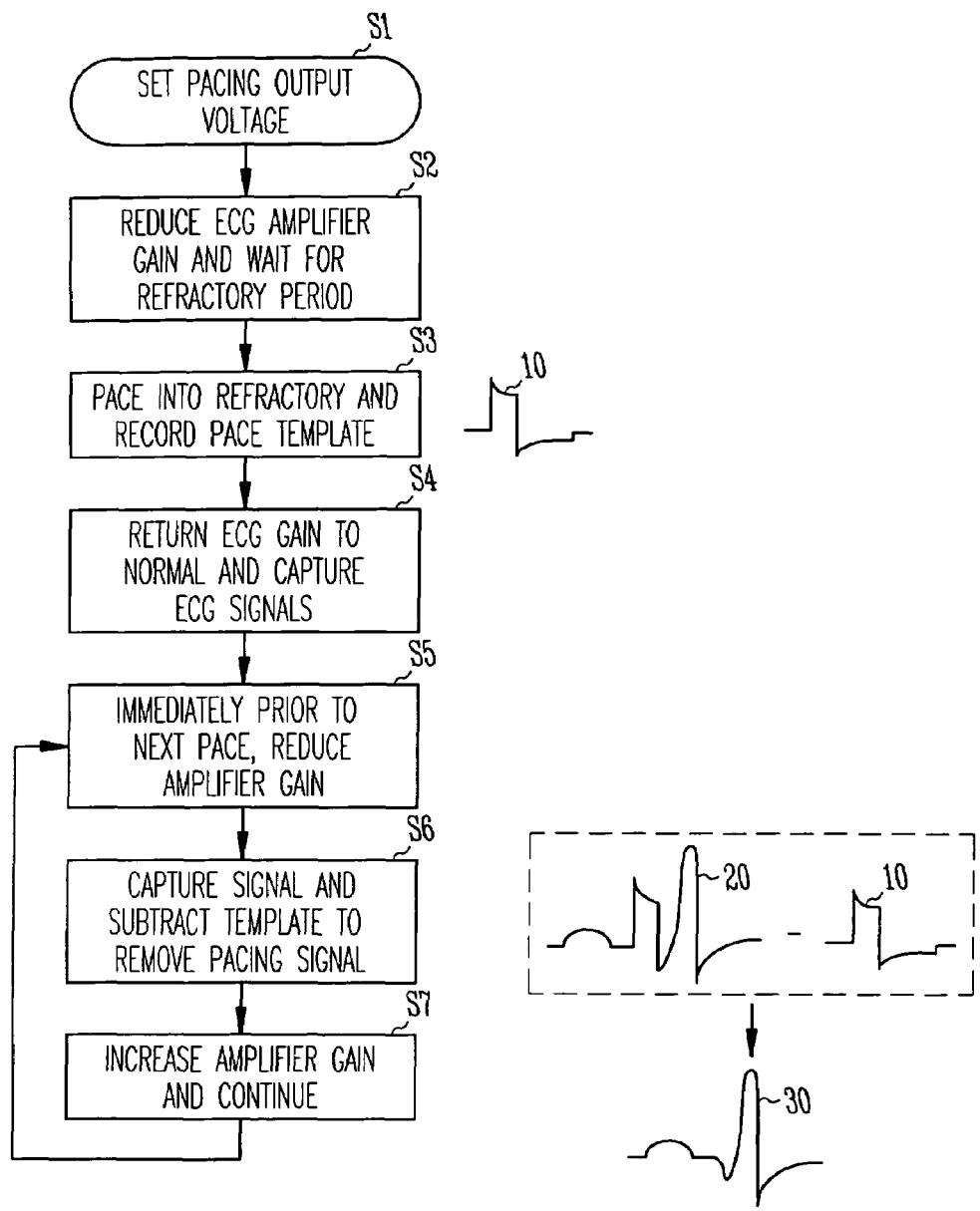
FIG. 3 illustrates an exemplary algorithm for removing pacing artifacts from electrograms.

FIG. 3 shows a flowchart diagram of an exemplary algorithm for removing pacing artifacts by an implantable pacing device. The device first acquires a template of the pacing pulse as received by the ECG electrode. After setting the pacing output voltage at step S1, the device waits for an appropriate pacing instant based upon sensed intrinsic activity at step S2 so that the pace is delivered when the paced chamber is refractory. Prior to a pacing pulse, the amplifier connected to the subcutaneous ECG channel is switched into an extremely low gain mode to avoid saturation due to the pacing pulse. At step S3, the pace is delivered during the refractory period, and the pacing template is recorded with the template being aligned to the pacing pulse. A representative template waveform 10 is shown in the figure. At step S4, the ECG amplifier gain is restored to normal in order to record electrogram signals during non-paced cycles. When a pace is subsequently to be delivered to capture cardiac tissue, the ECG amplifier gain is reduced immediately before each pace at step S5. At step S6, the evoked response electrogram is captured at the low-gain setting with the pace included as depicted by example waveform 20. The pacing template is then subtracted point for point from the electrogram signal after being aligned in time with the output pace to result in an electrogram signal with the pacing artifact removed as depicted by example waveform 30. After the pace, the amplifier is returned to its standard higher gain mode at step S7. The device then returns to step S5 to wait for another paced cycle.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac rhythm management device, comprising:
   one or more sensing channels for sensing intrinsic cardiac activity;
   a subcutaneous ECG channel incorporating a subcutaneous electrode for generating an electrogram referred to as a subcutaneous ECG signal;
   a pacing channel for pacing a cardiac chamber;
   a controller for controlling the delivery of pacing pulses in accordance with a programmed mode and recording electrograms from a sensing channel;
   wherein the controller is programmed to remove the pacing artifact from an electrogram generated by the subcutaneous ECG channel and recorded during a paced cardiac cycle by subtracting a pacing pulse template from the recorded electrogram, wherein the pacing pulse template is an electrogram recorded when a pace is delivered to a cardiac chamber while the chamber is refractory.

2. The device of claim 1 wherein the controller is programmed to align the pacing pulse template with the instant at which the pace is delivered during the paced cardiac cycle prior to subtracting the pacing pulse template from the recorded electrogram.

3. The device of claim 1 wherein the controller is programmed to insert a marker in the recorded electrogram after subtraction of the pacing pulse template indicating the pace delivered during the paced cardiac cycle.

4. The device of claim 1 wherein the controller is programmed to subtract samples of the pacing pulse template from corresponding samples of the recorded electrogram.

5. The device of claim 1 wherein the controller is programmed to subtract a sample of the pacing pulse template from a corresponding sample of the recorded electrogram as each sample of the recorded electrogram is acquired.

6. The device of claim 5 wherein the controller is programmed to wirelessly transmit a recorded electrogram from which pacing artifacts are removed in near real time.

7. The device of claim 1 wherein the controller is programmed to lower the gain of a sensing amplifier for recording an electrogram when a pace is delivered and process electrograms recorded during paced cycles in order to compensate for those electrograms being recorded at a lower gain setting than electrograms recorded during intrinsic cycles.

8. The device of claim 1 wherein the controller is programmed to remove the pacing artifact due to an atrial pace from an electrogram recorded during a cardiac cycle in which an atrial pace is delivered.

9. The device of claim 1 wherein the controller is programmed to remove the pacing artifact due to a ventricular pace from an electrogram recorded during a cardiac cycle in which a ventricular pace is delivered.

10. The device of claim 1 wherein the controller is programmed to generate the pacing pulse template by recording an electrogram when a pace is delivered to a cardiac chamber while the chamber is refractory.

11. A system for removing pacing artifacts from electrograms, comprising:
   an implantable device having a sensing channel for sensing intrinsic cardiac activity and a pacing channel for delivering pacing pulses to a cardiac chamber in accordance with a programmed mode;
   an external device in communication with the implantable device;
   wherein the implantable device is programmed to record an electrogram from a sensing channel and transmit the electrogram to the external device; and,
   wherein the external device is programmed to remove pacing artifacts from the electrogram by subtracting a pacing pulse template from the recorded electrogram during each paced cardiac cycle, wherein the pacing pulse template is an electrogram recorded when a pace is delivered to a cardiac chamber while the chamber is refractory.

12. The system of claim 11 wherein the pacing pulse template is generated by the implantable device and transmitted to the external device.

13. The system of claim 12 wherein the implantable device is programmed to generate the pacing pulse template by recording an electrogram when a pace is delivered to a cardiac chamber while the chamber is refractory.

14. The system of claim 11 wherein the external device is programmed to insert a marker in the recorded electrogram after subtraction of the pacing pulse template indicating the pace delivered during the paced cardiac cycle.

15. The system of claim 11 wherein the implantable device is programmed to lower the gain of a sensing amplifier for recording an electrogram when a pace is delivered and the system is programmed to process electrograms recorded during paced cycles in order to compensate for those electrograms being recorded at a lower gain setting than electrograms recorded during intrinsic cycles.

16. A system for removing pacing artifacts from electrograms, comprising:
   an implantable device having a sensing channel for sensing intrinsic cardiac activity and a pacing channel for delivering pacing pulses to a cardiac chamber in accordance with a programmed mode;
   an external device in communication with the implantable device;
   wherein the implantable device is programmed to record an electrogram from a sensing channel and transmit the electrogram to the external device; and,
   wherein the external device is programmed to remove pacing artifacts from the electrogram by subtracting a pacing pulse template from the recorded electrogram during each paced cardiac cycle, wherein the pacing pulse template is generated by the implantable device and transmitted to the external device.

17. The system of claim 16 wherein the external device is programmed to insert a marker in the recorded electrogram after subtraction of the pacing pulse template indicating the pace delivered during the paced cardiac cycle.

18. The system of claim 16 wherein the implantable device is programmed to lower the gain of a sensing amplifier for recording an electrogram when a pace is delivered and the system is programmed to process electrograms recorded during paced cycles in order to compensate for those electrograms being recorded at a lower gain setting than electrograms recorded during intrinsic cycles.

* * * * *